US00PP10049P

United States Patent [19]

Hartenhof

[11] Patent Number: Plant 10,049

[45] Date of Patent: Oct. 7, 1997

[54] APPLE TREE NAMED NS-911

[75] Inventor: Jacob A. Hartenhof, Waterville, Canada

[73] Assignee: Adams County Nursery, Inc., Aspers, Pa.

[21] Appl. No.: 393,207

[22] Filed: Jan. 25, 1995

[51] Int. Cl.[6] ..... A01H 5/00

[52] U.S. Cl. ..... Plt./34.1

[58] Field of Search ..... Plt./34.1

[56] References Cited

U.S. PATENT DOCUMENTS

P.P. 4,800 1/1982 LaMont ..... Plt./34.1
P.P. 5,095 8/1983 Nicklin ..... Plt./34.1

OTHER PUBLICATIONS

Brooks, R.M., et al. (Listing) "Cortland", *Register of New Fruit and Nut Varieties,* University of California Press, Berkeley, p. 24.

*Primary Examiner*—James R. Feyrer
*Attorney, Agent, or Firm*—Frank B. Robb; John H. Vynalek

[57] ABSTRACT

The tree of this disclosure is a newly discovered and stability tested color sport of the parent variety 'Cortland', which I have named 'NS-911'. The new tree is distinguished by having more highly colored fruit than that of 'Cortland' and 'Redcort', a color sport from the same source, and as having less conspicuous stripes within and masked by a solid blush which covers substantially the entire surface of the fruit. The ground color of fruit skin of each variety is substantially the same, but differs in terms of degree of coverage, with ground color patches being essentially absent from the surface of the fruit of 'NS-911'. The new tree is distinguished from 'Lamont' in having standard bearing and tree habit.

2 Drawing Sheets

BACKGROUND OF THE INVENTION

The variety 'Cortland' is an old variety, introduced in 1915, by S. A. Beach, N.Y. State Agricultural Experiment Station, which has been unusually popular in the market place. Because the fruit of the variety has exceptional attractiveness, pleasing taste and notable keeping qualities, it has been well accepted in the consumer market. Trees of the variety 'Cortland' are of exceptional hardiness and productivity; and, have been a popular variety in many old orchards throughout apple growing regions. Due to the premium market slot of the fruit of this tree, 'Cortland' has been widely planted and occupies a substantial area of apple tree production acreage in the apple producing areas of the United States, Canada and elsewhere. With large populations of trees planted to satisfy market demand for this exceptional fruit, as with many other popular varieties such as 'Red Delicious' and 'MacIntosh', numerous sports of 'Cortland' have been discovered over the years. These have been isolated and introduced, to a point where such related and improved trees share, and in some cases dominate, the market demand filled by the original 'Cortland' variety, and more successfully compete with fruit of other varieties in the marketplace. The overwhelming popularity of 'Cortland', and sports of this tree, has led to the development of its own market class, which over the years has been expanded to contain a number of related but competing trees. Introduction of improved sports has generally improved the quality of fruit available to the consumer as 'Cortland' in the market place.

The tree 'NS-911' is such an improvement. This tree was discovered by me as a limb sport on an old specimen of 'Cortland' growing in orchards under my control near Kentville, Nova Scotia, Canada. More specifically, it was initially noted because it produced a highly colored apple with a conspicuously more extensive and uniform red blush as compared to the fruit of adjacent 'Cortland' trees. The fruit of this sport is essentially totally red and uniform to an extent that the stripes which characterize the fruit skin color of most color sports of 'Cortland' all but disappear, by being masked by a heavy red blush, in the color expression of the fruit of this tree. Further, it was clear that the extent of the blush and the general lack of ground color on the fruit surface made the fruit of this tree most unusual. Because of the well established and recognized consumer preference for apples of solid red coloration, I immediately saw the distinction of this sport from trees of 'Cortland' near it; recognized the potential enhanced marketability of the fruit; and, I have observed in testing the fruit of the tree, that the tree also has retained the notorious high fruit flesh quality, flavor and keeping qualities of the parent 'Cortland' variety.

I have caused the tree to be reproduced asexually by budding, and find that it is in fact one which holds its characteristics through successive generations and produces apples of a decidedly attractive form, color, and taste.

In taste, fruit interior quality, texture, shape and keeping qualities, the apples of my tree 'NS-911' are not substantially different from those of 'Cortland' and known color sports thereof, such as 'Redcort'. However, the fruit of 'NS-911' has a more extensive and a more uniform red blush covering substantially all of the exterior of the apple. Only an occasional spot or patch of ground color occurs where fruit developed with its surfaces against a branch or was otherwise unusually shaded. This is in contrast to the fruit of 'Redcort' which expresses a red blush over distinctive stripes which are even more prominently visible over more extensive patches of green ground color. The blush and underlying stripes of 'Redcort' normally cover only about three quarters of the surface of the fruit.

The tree 'NS-911' is similar in habit to the parent 'Cortland'. It forms a standard tree size and is standard in bearing habit. Tree branching habit and canopy density are substantially identical to that of the parent tree; and has a similar spreading habit and scaffold branch placement. Mature bark colors of the oldest branch of the original sport is tan and bears a heavy pattern of large lenticels of cork-like texture and color, which are elongated in shape and in a generally horizontal pattern in attitude. Mature bark of the parent tree is shaggy and gray. Leaf characteristics of my new tree are substantially identical to those of the parent variety.

Figure 1:
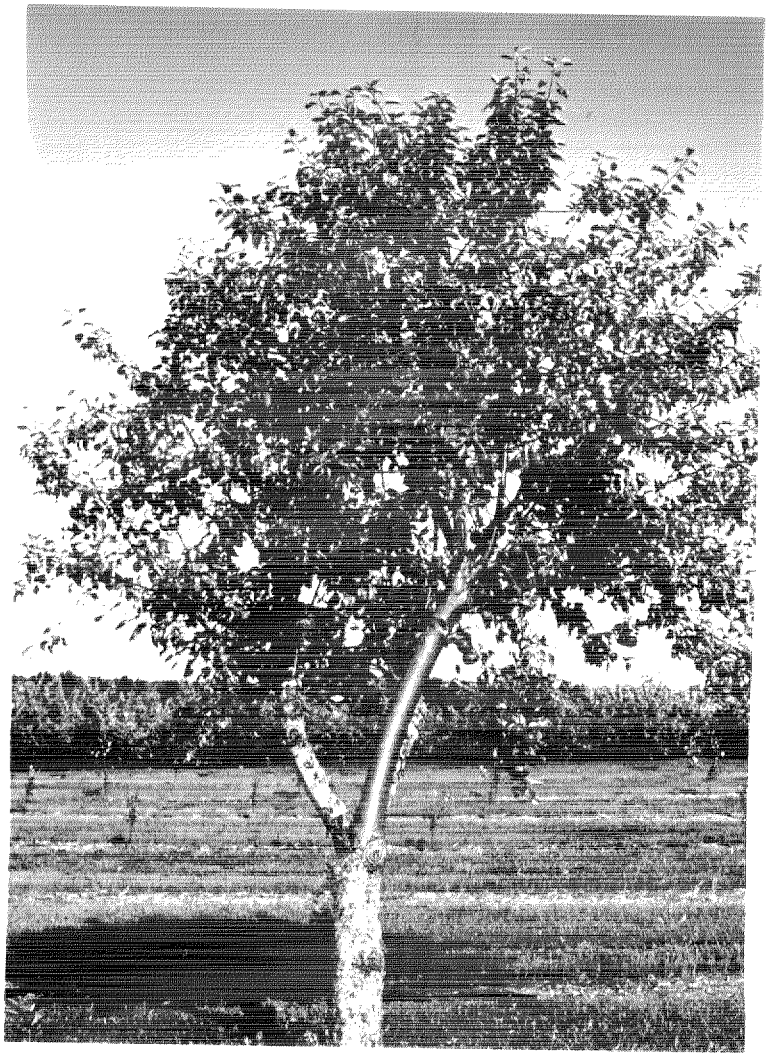
FIG. 1 depicts the original sport of the new variety 'S-911' growing on the original parent 'Cortland' tree. The ort is readily discernible by the distinctly different bark lor and texture. This drawing depicts the habit, canopy and af coloration which is substantially the same as that of the rent tree. The depicted specimen is shown with fruit at a age approaching harvest stage and shows the bearing habit the tree.
Figure 2:
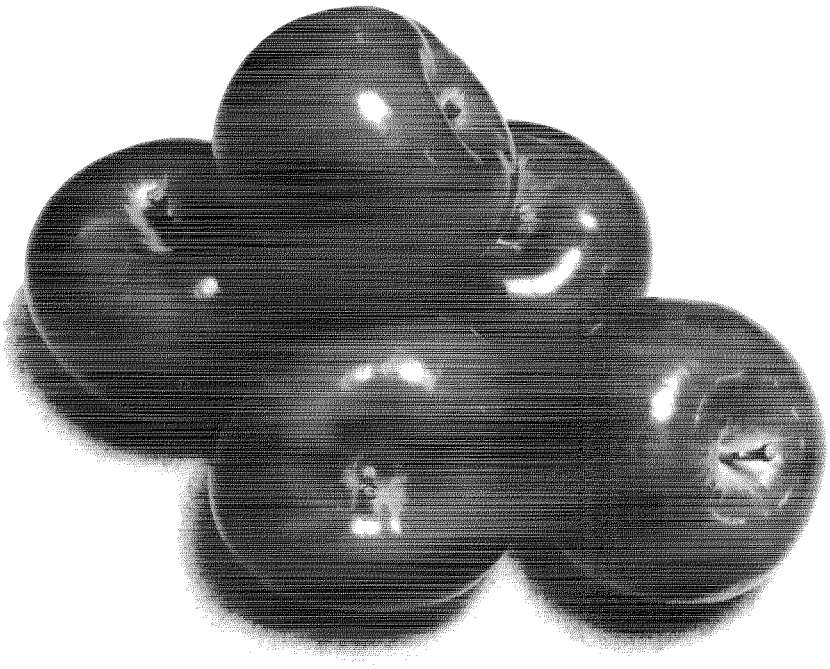
FIG. 2, shows five whole fruit of the new variety from the em end. Note that stripes are only faintly visible through very uniform, heavy attractive red blush. Fruit stems and e russetting within the stem basin are also depicted and milar to those of the parent 'Cortland'.
Figure 3:
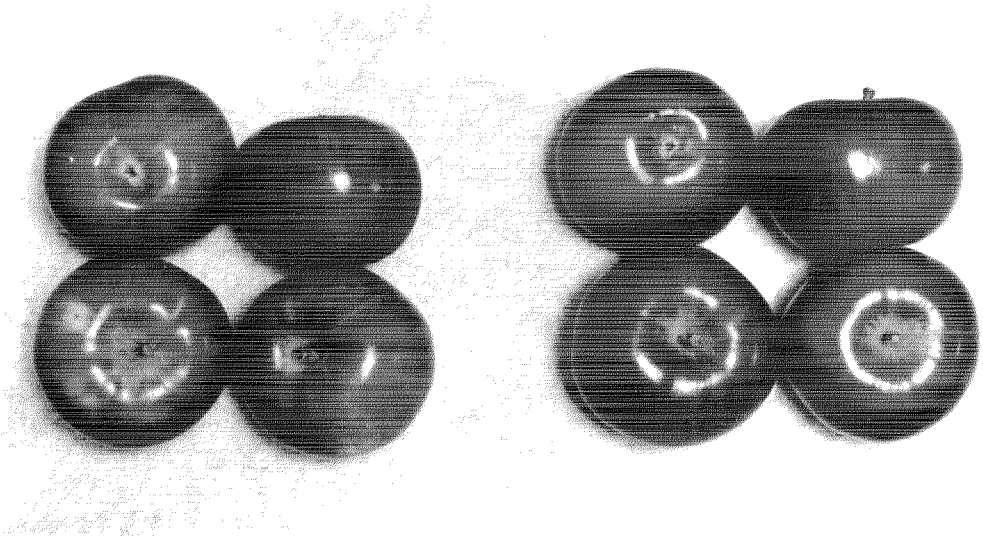
FIG. 3 illustrates, on the left, four specimens of fruit of the omparison variety 'Redcort'; and, on the right four speciens of 'NS-911' are shown. Specimens of each variety are ositioned to show the blossom end, side view, and stem nds of whole specimens of fruit of the comparison variety nd the new variety. The substantailly identical shape and ize of the fruit of both varieties are depicted. This comarison also shows that the stripes of 'Redcort' are more onspicuous than those of 'NS-911', and that 'Redcort' has much higher degree of ground color exposed beneath the lush. In contrast the surface of 'NS-911' is more completely nd more uniformly covered by a red blush which essenially masks the pattern of dark stripes.

The color descriptions presented in the botanical specifications to follow were taken from the color dictionary *Munsell Book of Color* except where general color values of ordinary dictionary significance are used.

DETAILED BOTANICAL DESCRIPTION

Botanic name strains: *Malus×domestica* a spontaneous color sport of the 'Cortland' variety. The name under which it will be known in commerce is Apple Tree 'NS-911'.

Tree:

*Size.*—Standard, approximately 14 feet high at maturity.

*Vigor.*—Medium.

*Form.*—Spreading. Low, open, rapid growing, hardy, very productive, and regular bearing.

*Trunk.*—Slender and smooth.

*Branches.*—Slender, smooth, many, brown with grey "bloom" color. Lenticels — Numerous and medium in size.

*Leaves.*—Length 10.5 cm; 4 1/16" Width 5.9; 2 5/16". Large, medium width, long, ovate, taper pointed, medium thickness, medium to dark green in color, and smooth. Margin — Crenate and coarsely serrate. Petiole — 1 5/16" in length, medium in length and thick. Stipules — Early deciduous.

*Flowers.*—Dates of first and full bloom — May 29 and June 03. Mid-time as compared with other varieties, medium size, and color is pink. Color bud 10RP4/14, balloon 7.5RP 5/10, flower 10RP 9/1.

Fruit:

*Maturity when described.*—Eating, date about Oct. 09. Uniform in size on MMIII Rootstock; slightly variable on M26. Axial diameter 2–2¼ inches. Transverse 2½–3 inches.

*Form.*—Variable; unsymmetrical. Oblique, oblate, and angular. Cavity — unsymmetrical, flaring toward apex, undulate, and depth less than ½" and breadth less than 1 5/16 inches. Markings — russet. Basin — Symmetrical, abrupt, wide base, furrowed, and glabrous.

*Stem.*—Stout, pubescent, length less than ½", and bracts occasionally present and numbering 2.

*Calyx.*—Closed, segments persistent, broadly lanceolate, acute, and length varying about 5/16 inches imbricate at base, ascending, converged at apex, outer and inner surface pubescent.

*Eye.*—Medium and closed.

*Skin.*—Smooth, glossy, waxed, dots are obscure but many, small, even, depressed and circular. Color of dots grey and distribution uniform. Ground color — green-yellow 2.5 GY 8/8. Color markings — self-colored and dull. Color of markings — burgundy red, 2.5R 2/6. Bloom — abundant. General color effect — red overall.

*Flesh.*—Rather juicy. Color of flesh — satiny and white. Texture — firm, coarse, and crisp. Flavor — subacid and sprightly. Aroma — distant. Quality — good.

*Core.*—Sessile — distant. Bundle area — (longitudinal section) large, broadly, ovate, symmetrical at base, alternate, with cells. Halves of area equal. Bundles green, inconspicuous, and one whorls. Alternate bundle approximate to distant from calyx tube, reaches tube at below stamens. Core lines meeting, carpellary area distinct and large. Calyx tube — pubescent, broadly cone-shaped, stem of funnel is short, depth of tube to shoulder 3/16 inch, entire depth ¼ inch. Axiallary cavity wanting. Seed cells — axile and open. Cell walls — thick, length ⅝ inches, breadth ⅜ inches. Longitudinal section is broadly ovate and acute. Entire surface is smooth. Cross section is broad.

Seeds: Number perfect 5, Imperfect 3.

*Largest number in one cell.*—2, length ¼ inches.

*Breadth.*—⅛ inch.

*Form.*—Acute.

*Color.*—10YR 3/4.

Use: Market and dessert.

Keeping quality: Good. Number of days in ordinary storage is at least 150.

Resistance to:

*Insects.*—Aphids is not very outstanding, but similar to 'Stewart' and 'Redcort'. Insect and disease reactions are not different from 'Stewart', 'Starkspur', and 'Redcort' grown in the same area.

I claim:

1. A new and distinct Apple Tree substantially as herein shown and described, characterized particularly as to novelty by more extensive and more uniform red blush covering substantially all of the exterior of the fruit with only an occasional patch of ground color.

* * * * *